United States Patent [19]

Jelly

[11] Plant 4,152

[45] Nov. 15, 1977

[54] WHITE ROSE PLANT SEEDLING

[75] Inventor: Robert G. Jelly, Richmond, Ind.

[73] Assignee: E. G. Hill Co., Inc., Richmond, Ind.

[21] Appl. No.: 765,397

[22] Filed: Feb. 3, 1977

[51] Int. Cl.[2] ..... A01H 5/00

[52] U.S. Cl. ..... Plt./14

[58] Field of Search ..... Plt./14, 23

*Primary Examiner*—Robert E. Bagwill

*Attorney, Agent, or Firm*—Chas. W. Rummler

[57] ABSTRACT

A white rose cultivar most suitable for greenhouse culture for cut flower production, the new plant being distinguished by its abundant and continuous production of small white flowers borne on long, moderately strong stems, its extraordinary vigor as a greenhouse rose which permits a greater spacing of the plants and an improvement in the economics of rose plant costs, and by the good vase life of its flowers.

1 Drawing Figure

BACKGROUND OF THE NEW PLANT

This new variety of rose plant originated at Redwood City, Calif., as a seedling resulting from my crossing of an undisseminated seedling, identified as number 9-6-7-PS in my breeding stock, with the cultivar Bridal Pink (U.S. Plant Pat. No. 2,851) as the pollen parent in the Spring of 1969. My object was to improve the keeping quality of Bridal Pink and to improve the stem length of the seed parent and the new variety, although white and not the pink of its parents, has the characteristics that I was seeking. The first flowering of this new rose variety occurred in 1970 and because of its distinctiveness over its parents, I reproduced the plant by grafting to test its retention of its distinguishing characteristics. Propagation of this new plant through successive generations, by grafting at Richmond, Ind., and by budding at Livermore, Calif., has demonstrated that the distinctive characteristics of the new variety hold true from generation to generation and appear to be firmly fixed.

DESCRIPTION OF THE DRAWING

My new variety of white rose plant is illustrated by the accompanying photographic drawing which shows, in full color, face views of a newly opened flower and a mature blossom, specimens of buds in various stages of opening, typical specimens of leaves, a specimen of young wood with leaves, and a specimen of the mature wood. The colors shown are believed to be as true as is reasonably possible to be had through conventional photographic procedures.

DESCRIPTION OF THE NEW PLANT

The following is a detailed description of my new variety of white rose plant based upon observations of greenhouse plants made at Richmond, Ind., the color designations being made according to the Horticultural Colour Chart (HCC) produced by Robert S. Wilson in collaboration with the British Color Council and according to the Royal Horticultural Society Colour Chart (RHS), both having been published by The Royal Horticultural Society of London, England.

THE PLANT

Origin: Seedling identified as No. 72-72-WS.

Parentage:

*Seed parent.*—Undisseminated Seedling No. 9-6-7-PS.

*Pollen parent.*—Bridal Pink (P.P. 2,851).

Classification: Floribunda.

Type: For greenhouse culture for cut flower production.

Form: Bush.

Growth: Vigorous and moderately free.

Habit: Upright and much branched.

Canes: Medium in diameter.

Main stems: Color — A shade between Yellow Green 144 A (RHS) and Yellow Green 143 B (RHS).

*Thorns.*—Few, of medium length, straight and angled slightly downward from a short, broad base. Color: Greyed-Orange 165 A (RHS) at the base, pencilled with Greyed-Orange 174 A (RHS) shaded to Greyed-Orange 166 C (RHS) at the tip.

*Prickles and hairs.*—None.

Branches: Color — Green Group 143 A (RHS) pencilled with Green Group 137 B (RHS).

*Thorns.*—Very few, of medium length, straight and angled slightly downward from the base, some of which are short and some medium long. Color: Greyed-Orange 177 D (RHS) at the base shaded to an almost translucent hue of Yellow Green 147 D (RHS) at the tip.

*Prickles.*—Very few. Color: A translucent shade between Yellow Green 147 C (RHS) and Yellow Green 147 D (RHS).

*Hairs.*—None.

Foliage:

*Quantity.*—Moderately abundant.

*Leaves.*—Compound and odd pinnate. Size: Normally small to medium.

*Leaflets.*—5 to 7. Shape: Ovoid with cuspidate apex, obtuse base, and serrate margin. Color: Young Leaves: Upper surface — Yellow Green 144 B (RHS) on both sides of the mid-vein, shaded to a blend of Greyed-Purple 187 B (RHS) and Greyed-Purple 183 B (RHS) along the margin and mid-vein. Under surface — A shade between Greyed-Red 182 B (RHS) and Greyed-Red 182 C (RHS). Mature leaves: Upper surface — Yellow Green 145 A (RHS) down the mid-vein with an overall color of Green 137 A (RHS). Under surface — Spinach Green 0960/3 (HCC).

*Rachis.*—Medium in size. Upper Side: Heavy and prickly. Under Side: A few with thorns.

*Stipules.*—Wide and short to medium in length with short points turning out at an angle of slightly more than 45°.

THE BUD

Before calyx breaks:

*Size.*—Small to medium small.

*Form.*—Short pointed with conspicuous neck and with foliaceous appendages on the surface of the bud having slender bristle-like parts extending beyond the tip of the bud equal to one-fourth to one-half or more of the bud length.

*Color.*—The mid-line of the sepals is Yellow Green 145 A (RHS) shaded through Yellow Green 144 B (RHS) to Green 143 B (RHS) on the margins and foliaceous parts.

As the calyx breaks:

*Outside petal color.*—Green Yellow 1 D (RHS).

As first petal opens:

*Bud size.*—Medium small.

*Bud form.*—Short pointed.

*Color of petal.*—Outside — Green White 157 C (RHS). Inside — Green Yellow 1 C (RHS) at the base to the main petal color of Green White 157 C (RHS).

Character of opening: The bud opens well in the greenhouse.

Effect of weather: The bud is slightly smaller in size in hot, dry weather.

Sepals: Permanent and of medium length.

*Shape.*—Spear shaped with a wide base. When calyx breaks, sepals spread outwardly and then extend in a substantially horizontal manner from the calyx as the bud opens.

*Color.*—Inside — Yellow Green 145 D (RHS) along the mid-vein shaded to a velvety hue of Green 141 C (RHS). Outside — Yellow Green 145 B (RHS) along the mid-vein to a shade between Green 143 B and 143 C (RHS).

Peduncle:

*Size.*—Strong and erect, short and of medium diameter.

*Bark.*—Entirely smooth. Color: A shade slightly darker than Yellow Green 144 A (RHS).

*Thorns.*—None.

*Prickles.*—Few. Color: From Yellow Green 144 D (RHS) at the base to almost translucent at the tip.

*Hairs.*—Few. Color: Yellow Green 144 C (RHS) with a bulb-like end of Greyed-Purple 185 B (RHS).

THE FLOWER

Blooming Habit: Free, abundant and continuous, in greenhouse.

Size: Small when fully opened — 2½ to 3 inches in diameter.

Form: High centered, with petals loosely rolled outward at first and becoming very tightly rolled outward at maturity.

Borne: One to a stem on moderately strong and long stems.

Petalage: Very double, with 29 to 33 petals regularly arranged.

*Shape.*—Outside petals — Obovate with cuspidate apex. Intermediate petals — Obovate with obtuse apex. Inside petals — Obovate with flat apex.

*Texture.*—Moderately thick and leathery.

*Appearance.*—Satiny on both inside and outside surfaces.

Color:

The following is the color description of a newly opened greenhouse rose in the month of June, 1976:

*Outside petals.*—Outer surface — Yellow Green 154 D (RHS) at the base shaded to the main color of White 155 C (RHS). Inside surface — A shade between Yellow Green 154 C and Yellow Green 154 D (RHS) at the base to the main color of White 155 B (RHS).

*Intermediate petals.*—Outer surface — Green Yellow 1 D (RHS) at the base shaded to the main color of Green White 157 D (RHS). Inside surface — Green Yellow 1 D (RHS) at the base shaded to the main color of Green White 157 D (RHS).

*Inner petals.*—Outside surface — A shade between Green Yellow 1 C and Green Yellow 1 D (RHS) shaded to the main color White 155 A (RHS). Inside surface — Yellow Green 154 D (RHS) at the base shaded to the main color of White 155 A (RHS).

This description was made from observations of a rose that was fully open for three days in greenhouse in the month of June, 1976.

*Outside petals.*—Outer surface — Yellow Green 145 B (RHS) at the base shaded to the main color of White 155 C (RHS). Inside surface — Green Yellow 1 D (RHS) at the base shaded to the main color of White 155 B (RHS).

*Intermediate petals.*—Outer surface — A shade between Green 142 C and Green 142 D (RHS) at the base shaded to the main color of Green 155 B (RHS). Inside surface — A shade between Yellow Green 149 D and Yellow Green 150 D (RHS) at the base shaded to the main color of White 155 D (RHS).

*Inner petals.*—Outer surface — Yellow Group 4 D (RHS) at the base shaded to the main color of White 155 D (RHS). Inside surface — Yellow 2 D (RHS) at the base shaded to the main color of White 155 B (RHS).

General color effect: Newly opened flower — White 155 D (RHS). Three days opened flower — White 155 B (RHS).

Note: The colors described may be modified by being shaded with other colors.

Fragrance: Slight sweetbriar.

Persistence: Petals hang on and dry.

Effect of weather: The bud and flower are slightly smaller in hot, dry weather.

Lasting quality: Seven days at living room temperature (observed in November 1975).

REPRODUCTIVE ORGANS

Stamens: Regularly arranged about the pistils and mixed with a few petaloids.

*Filaments.*—Lengths vary from short to long, most with anthers. Color: Green White 157 B (RHS).

*Anthers.*—Medium in size. All open at once. Color: Some Greyed-Orange 163 A (RHS) and some Greyed-Orange 163 B (RHS).

*Pollen.*—Moderate in quantity. Color: Greyed-Orange 163 B (RHS).

Pistils: Medium in number.

*Styles.*—Length — Uneven, medium to long. Moderately thin in diameter, very bunched and mixed with filaments. Color: A shade slightly lighter than Greyed-Yellow 160 C (RHS).

*Stigmas.*—Color — Green White 157 A (RHS).

Ovaries: Some protruding from calyx.

Seeds: Small and of average number.

This new rose variety differs from its pink parents, in particular, because it is white. It has maintained from its seed parent a very unusual vigor for greenhouse roses and by virtue of its extreme vigor it can be planted further apart thus aiding in the reduction of rose plant costs. Also, this variety is superior to its pollen parent.

I claim:

1. A new and distinct variety of rose plant substantially as herein shown and described, characterized by its abundant and continuous production of white blossoms of relative small size but excellent form, borne on long, moderately strong stems, and by its extraordinary vigor for a greenhouse rose.

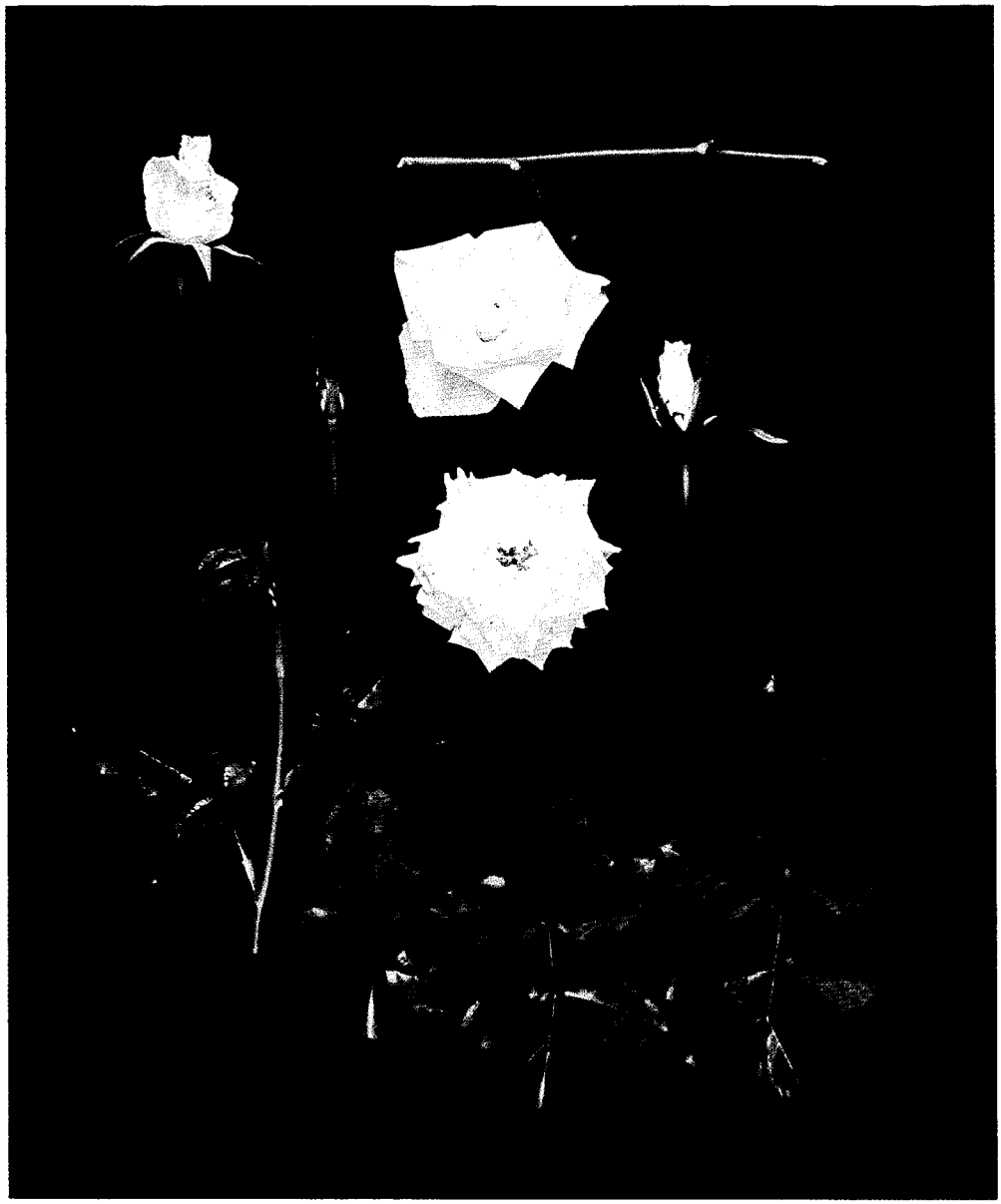

* * * * *